United States Patent
Kim

(10) Patent No.: US 7,976,215 B2
(45) Date of Patent: Jul. 12, 2011

(54) APPARATUS AND METHOD FOR MEASURING THERMAL DIFFUSIVITY USING THE FLASH METHOD

(75) Inventor: Seog Kwang Kim, Daejeon (KR)

(73) Assignee: Korea Advanced Institute of Science and Technology (KR)

(*) Notice: Subject to any disclaimer, the term of this patent is extended or adjusted under 35 U.S.C. 154(b) by 494 days.

(21) Appl. No.: 12/108,957

(22) Filed: Apr. 24, 2008

(65) Prior Publication Data
US 2009/0110025 A1 Apr. 30, 2009

(30) Foreign Application Priority Data
Oct. 26, 2007 (KR) .................. 10-2007-0108123

(51) Int. Cl.
G01K 1/00 (2006.01)
(52) U.S. Cl. ............................. 374/7; 374/43; 374/121
(58) Field of Classification Search ............... 374/7, 121, 374/43
See application file for complete search history.

(56) References Cited

U.S. PATENT DOCUMENTS

| | | | |
|---|---|---|---|
| 4,928,254 A * | 5/1990 | Knudsen et al. | 702/136 |
| 6,273,603 B1 * | 8/2001 | Cheindline et al. | 374/43 |
| 6,375,349 B1 * | 4/2002 | Gaal et al. | 374/44 |
| 2006/0039443 A1 * | 2/2006 | Watanabe et al. | 374/44 |
| 2006/0153269 A1 * | 7/2006 | Lakestani et al. | 374/43 |
| 2010/0062220 A1 * | 3/2010 | Nishikawa | 428/156 |

OTHER PUBLICATIONS

Sin Chul Bae et al., Journal of Korean Society of Mechanical Engineers, vol. 14, p. 157-171 (1990).

G. E. Young Blood et al., "Thermal Diffusivity of Partially and Fully Stabilized (Yttria) Zirconia Single Crystals", J. Am. Cerurn. Soc., 71 141, 1988. pp. 255-260.

Abderrahmane Baïri, "Analytical model for thermal resistance due to multiple moving circular contacts on a coated body", C. R. Mecanique 331, 2003, pp. 557-562.

Seog-Kwang Kim et al., "Determination of apparent thickness of graphite coating in flash method", Thermochimica Acta 468, 2008, pp. 6-9.

W. J. Parker, et al., "Flash Method of Determining Thermal Diffusivity, Heat Capacity, and Thermal Conductivity", Journal of Applied Physics vol. 32, No. 9, Sep. 1961, pp. 1679-1684.

Seog-Kwang Kim et al, "Improvement of specific heat measurement by the flash method" ,Thermochimica Acta 455, 2007, pp. 30-33.

E. Litovsky et al., "Non-destructive Thermal Diagnostics of Porous Materials", International Journal of Thermophysics, vol. 26, No. 6, Nov. 2005, pp. 1815-1831.

(Continued)

Primary Examiner — Lisa M Caputo
Assistant Examiner — Mirellys Jagan
(74) Attorney, Agent, or Firm — Momkus McCluskey, LLC; Jefferson Perkins

(57) ABSTRACT

The present invention relates to an apparatus and method for measuring thermal diffusivity using the flash method. The apparatus includes: a laser generator 60 for generating a flash beam 30; a measurement sample 10 having graphite layers 20 formed on front and rear surfaces thereof, through which the flash beam 30 passes; an infrared sensor 70 disposed at the rear of the measurement sample 10 for measuring a temperature and time at the rear surface of the measurement sample 10 from heat 40 dissipated from the measurement sample 10; and operation means 80 for performing an operation based on an output signal of the infrared sensor 70.

9 Claims, 4 Drawing Sheets

OTHER PUBLICATIONS

N. D. Milos Evic et al., "Simultaneous Estimation of the Thermal Diffusivity and Thermal Contact Resistance of Thin Solid Films and Coatings Using the Two-Dimensional Flash Method", International Journal of Thermophysics, vol. 24, No. 3, May 2003, pp. 799-819.

J. A. Cape et al., "Temperature and Finite Pulse-Time Effects in the Flash Method for Measuring Thermal Diffusivity", Journal of Applied Physics vol. 34, No. 7, Jul. 1963, pp. 1909-1913.

F. Cernuschi et al., "The effects of sample surface treatments on laser flash thermal diffusivity measurements", Infrared Physics & Technology 43, 2002, pp. 133-138.

Korean Intellectual Property Office, English translation of office action issued on Korean Patent Application No. 10-2007-0108123 dated Mar. 25, 2009.

* cited by examiner

APPARATUS AND METHOD FOR MEASURING THERMAL DIFFUSIVITY USING THE FLASH METHOD

BACKGROUND OF THE INVENTION

1. Field of the Invention

The present invention relates to an apparatus and method for measuring thermal diffusivity using the flash method, and more particularly, to an apparatus and method for measuring thermal diffusivity using the flash method, in which the thermal diffusivity of a sample can be measured accurately using the method of determining the resistance factor of coated graphite on the sample and measuring the apparent thickness of the coated sample.

2. Background of the Related Art

The accurate measurement of thermo-physical properties such as thermal diffusivity, specific heat and thermal conductivity is of prime importance in heat transfer analysis and application technologies in engineering. Especially, as new highly functional solid material and heat transfer medium are fast exploited with rapidly developing industries, establishment of a reliable and accurate measurement technique of the thermo-physical properties is highly demanding.

In the conventional thermal conductivity measurement technique in a steady state, the contact resistance between the test sample and the measuring tool causes non-negligible error, and the conventional measurement requires relatively long measurement time. In contrast, since the flash method is a non-contact method, the thermal diffusivity is measured in a short time, the sample size can be made small and it is easy to acquire the data. In addition, it enables the diffusivity measurement in a wide temperature range from room temperature to 2,000 degrees Celsius.

Graphite coating of sample is a process that is fundamental in thermal diffusivity measurement by the flash method. It increases both the absorbance of flash energy on the front surface and the intensity of the infrared light which is emitted from the rear surface. Moreover, the graphite coating plays an important role in decreasing the surface roughness. However, the additional graphite coating increases the thermal resistance of the sample. This has become the most critical factor of an error occurring when measuring the thermal diffusivity.

As a solution to this problem, Hasselman, et al. recommends that materials with a high thermal diffusivity, such as aluminum, must have an ideal thickness of 3 mm or more and every measurement sample must have an optimal thickness. However, according to this method, it is practically impossible to set an optimal thickness for every material because there is a need for the development of new materials and special functional materials with excellent thermal characteristics in these days.

Further, as an alternative solution to this problem, there were presented theories and experimental equations for measuring the thermal resistance of the coated graphite. However, the theories and experimental equations are not compatible with actually obtained experimental data. This makes it difficult to apply the theories and experimental equations to actual material designs.

FIG. 1 is a perspective view showing a conventional thermal diffusivity measurement device 100. The thermal diffusivity measurement device 100 largely includes, as shown in FIG. 1, the first and second sample holder plates 12 and 14, sample holders 16, a measurement sample 10, a sample cover 18 and peripheral measurement units.

The sample holder 16 is a member for holding the measurement sample 10. The sample holder 16 is made of steel materials and is placed between the second sample holder plates 12. The first sample holder plates 12 are positioned on the second sample holder plates 14 on both sides of the sample holder 16, thus fixing the sample holder 16.

Further, the sample cover 18 is placed on the sample holder 16 such that it can be opened or closed when the measurement sample 10 is inserted into or withdrawn from the sample holder 16. If a flash beam 30 is generated from a laser generator 60 in a state where the measurement sample 10 is disposed as described above, the flash beam 30 heats the measurement sample 10. This thermal diffusivity measurement device 100 is constructed to maintain an insulation state, and hence heat 40 dissipated from the measurement sample 10 is incident on an infrared sensor 70.

An output signal of the heat 40 dissipated from the infrared sensor 70 as described above is input to operation means 80 and is used to measure a half time. This operation means 80 are embedded software for detecting the output signal to calculate a half time and calculating thermal diffusivity on the basis of the operation result.

FIG. 2 is a graph showing a process of measuring a temperature change in the infrared sensor 70 as time elapses in the prior art. As shown in FIG. 2, a temperature measured in the measurement sample 40 shows a minute change at an early stage and, after a lapse of a certain time period, it reaches the highest temperature $T_{max}$ of the measurement sample 40. In this case, regarding the state of the measurement sample 10, it can be said that a temperature rise by the incoming flash beam 30 and a temperature drop by the outgoing heat 40 are in an equilibrium state. The time required for the half of the temperature rise to reach the thermal equilibrium is called the half time $t_{1/2}$.

Equation (1) may represent a temperature rise at the rear surface of the measurement sample 10 according to a heating time, $$\frac{\Delta T}{\Delta T_{max}} = 1 + 2\left[\sum_{n=0}^{\infty}(-1)^2 \exp(-n^2 2\pi^2 \alpha t l_s^{-2})\right] \quad (1)$$

where $\alpha$ and $l_s$ denote the thermal diffusivity $\alpha$ and the thickness of the measurement sample 10, respectively. $\Delta T$ denotes a temperature rise according to the time at the rear surface of the measurement sample 10 and $\Delta T_{max}$ denotes the peak level of a temperature rise at the rear surface of the measurement sample 10. Further, t denotes the illumination time of the flash beam.

A half of the time at which temperature rise $\Delta T$ at the rear surface of the measurement sample 10, after radiating the flash beam 30, reaches the thermal equilibrium state $\Delta T_{max}$ is called the half time $t_{1/2}$. Further, the thermal diffusivity can be found according to Equation (2).

$$\alpha = \frac{0.138785 l_s^2}{t_{1/2}} \quad (2)$$

However, as mentioned above, if precise data of the thickness $l_s$ of the graphite layer is not obtained, there was a problem in that error occurs in the value of the thermal diffusivity.

SUMMARY OF THE INVENTION

Accordingly, the present invention has been made in view of the above problems occurring in the prior art, and it is the first object of the present invention to provide an apparatus and method, which can measure thermal diffusivity with precision and reproducibility by reflecting the thermal resistance value of a coated sample in the thickness of the sample.

It is the second object of the present invention to show a simple method of predicting the apparent thickness of this coated graphite.

It is the third object of the present invention to induce a correlation function for the resistance coefficient, which is the ratio of the apparent thickness and the thickness of graphite coating.

Further characteristics, specific merits and novel characteristics of the invention will become more apparent from the following detailed description and exemplary embodiments taken in conjunction with the accompanying drawings.

To accomplish the above objects, in one aspect, the present invention provides a thermal diffusivity measurement device 100 employing the flash method including: a laser generator 60 for generating a flash beam 30; a measurement sample 10 having graphite layers 20 formed on the front and rear surfaces thereof, through which the flash beam 30 passes; an infrared sensor 70 disposed at the rear of the measurement sample 10 for measuring a temperature and time at the rear surface of the measurement sample 10 from heat 40 dissipated from the measurement sample 10; and operation means 80 for performing an operation based on an output signal of the infrared sensor 70.

In particular, the measurement sample is supported by sample holders and covered with a sample cover to thereby maintain a insulation state.

In particular, the operation means calculates a resistance coefficient and an apparent graphite thickness of the measurement sample based on an output signal of the infrared sensor.

In particular, each of the graphite layers respectively formed on the front and rear surfaces of the measurement sample has a thickness of 10 μm to 40 μm.

In particular, the graphite layers respectively formed on the front and rear surfaces of the measurement sample are coated with graphite spray.

To accomplish the above objects, in another aspect, the present invention provides a method of measuring thermal diffusivity using the flash method including: a step (S10) of coating a measurement sample with graphite through spray to thereby form graphite layers; a step (S20) of measuring a thickness and weight of the graphite-coated measurement sample; a step (S30) of calculating a thickness of the formed graphite layer based on the measured thickness and weight of the measurement sample; a step (S40) of calculating a half time with respect to the graphite-coated measurement sample; a step (S50) of calculating a resistance coefficient of the measurement sample whose half time has been calculated; a step (S60) of calculating an apparent graphite thickness based on the resistance coefficient; and a step (S70) of calculating a thermal diffusivity based on the apparent graphite thickness.

In particular, in the step (S40), the half time is experimentally calculated from a temperature rise graph at the rear surface of the measurement sample depending on the time.

In particular, in the step (S50), the resistance coefficient is calculated by the following Equation (6):

$$Gr_{eff} = 4.2454(t_{1/2})^{-0.465}. \quad (6)$$

In particular, in the step (S60), the apparent thickness is calculated by the following Equation 4:

$$Gr_{eff} = \frac{l_{apgr}}{l_{gr}}. \quad (4)$$

In particular, in the step (S70) of calculating the thermal diffusivity, the thermal diffusivity is calculated by the following Equation 5:

$$\alpha = \frac{0.138785 \ (l_s + l_{apgr})^2}{(t_{s+gr})_{1/2}}. \quad (5)$$

BRIEF DESCRIPTION OF THE DRAWINGS

Further objects and advantages of the invention can be more fully understood from the following detailed description taken in conjunction with the accompanying drawings in which.

Figure 1:
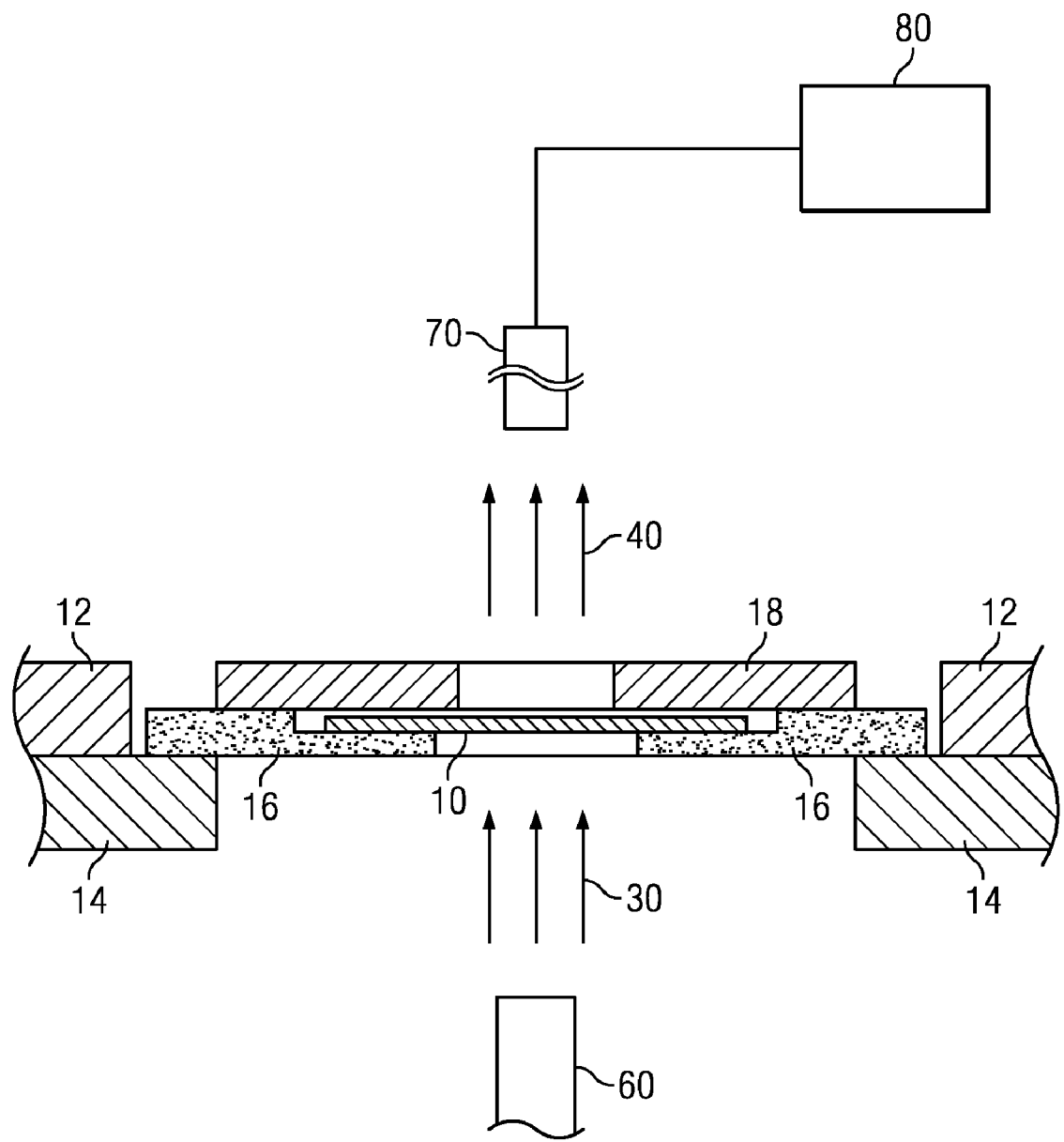
FIG. 1 is a perspective view showing a conventional thermal diffusivity measurement device.
Figure 2:
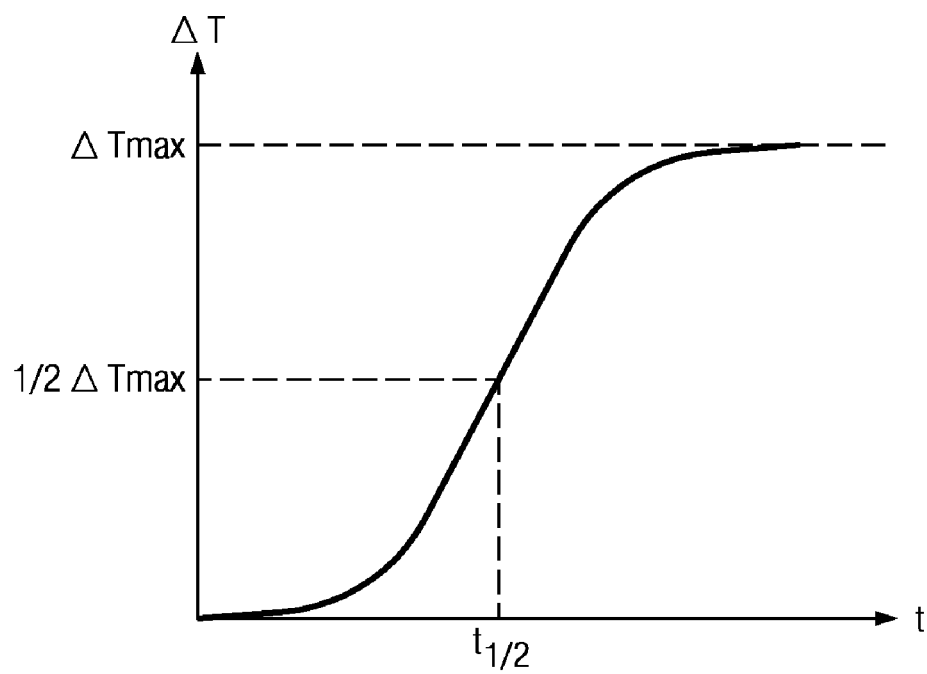
FIG. 2 is a graph showing a process of measuring a temperature change in an infrared sensor as time elapses in the prior art.

<Description of Reference Numerals of Principal Elements in the Drawings>

| | |
|---|---|
| 10: measurement sample | 12: first sample holder plate |
| 14: second sample holder plate | 16: sample holder |
| 18: sample cover | 20: graphite layer |
| 30: flash beam | 40: heat |
| 50: sample coated with graphite layer | 60: laser generator |
| 70: infrared sensor | 80: operation means |
| 100: thermal diffusivity measurement device | |

DETAILED DESCRIPTION OF THE PREFERRED EMBODIMENT

The present invention will now be described in detail in connection with specific embodiments with reference to the accompanying drawings.

Figure 3:
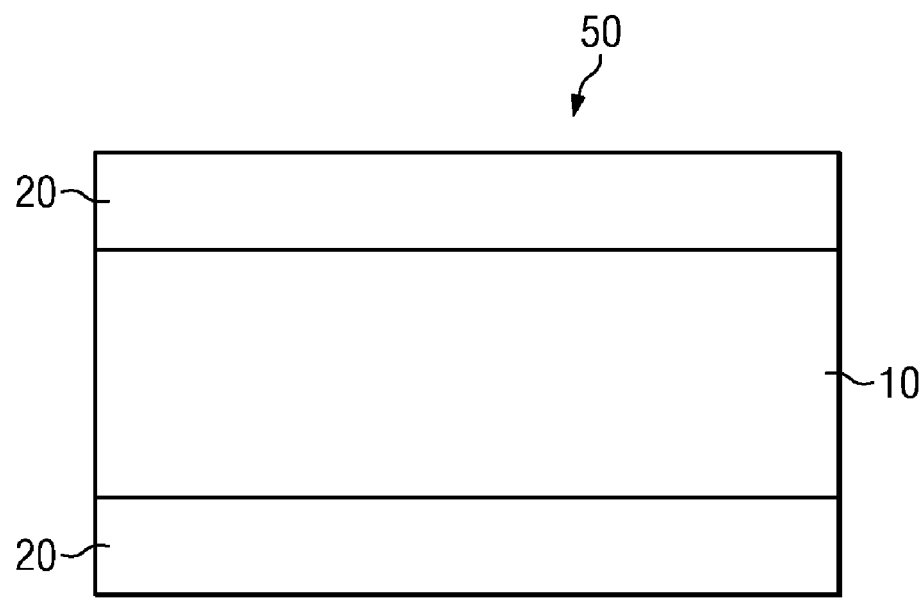
FIG. 3 is a sectional view showing a state where both sides of a sample are coated with graphite according to the present invention.

FIG. 3 is a sectional view showing the construction of a measurement sample 10 according to the present invention. As shown in FIG. 3, the front and rear surfaces of the measurement sample 10 are surrounded by a graphite layer 20. If the measurement sample 10 is formed as described above, the flash beam 30 incident on the front surface of the measurement sample 10, as shown in FIG. 1, is dissipated as the heat 40 at the rear surface of the measurement sample 10 as the temperature of the measurement sample 10 rises.

In the thermal diffusivity measurement device 100 according to the present invention, the measurement sample 10 is insulated by the sample holder 16, the first and second sample holder plates 12, 14, and the sample cover 18 so that the heat dissipated from the measurement sample 10 is not emitted to other portions, as shown in FIG. 1.

Further, as described above, a temperature rise depending on the time, of the heat 40 dissipated from the rear surface of the measurement sample 10, is detected by the infrared sensor 70.

Further, an output signal output from the infrared sensor 70 is input to the operation means 80 and calculated by a predetermined software embedded in the operation means 80. Operations of Equation 3 to Equation 6 are performed in the operation means 80. Although not shown in the drawings, the thermal diffusivity measurement device 100 of the present invention is constructed to display the measurement result of thermal diffusivity according to the operation result within a short time. Details of this display are evident to those having ordinary skill in the art and description thereof is omitted.

In particular, the thermal diffusivity measurement device 100 using the flash method according to the present invention can employ a laser flash apparatus (LFA).

Here, the reason why graphite is selected is that graphite can increase the intensity of infrared ray emitted from the rear surface of the measurement sample 10 and reduce the surface roughness of the measurement sample 10. However, if the material such as graphite is coated on the surface of the measurement sample 10 and the thermal diffusivity α is measured, a great error is generated as described above.

The cause of this error is that the thickness $l_s$ of the measurement sample 10 was calculated without considering the thickness $l_{gr}$ of the graphite layer 20, acting as thermal resistance, when considering the thermal diffusivity from the thickness $l_s$ of the sample in Equation 2.

The thickness $l_{gr}$ of the graphite layer 20 can be calculated according to Equation 3.

$$l_{gr} = \frac{m_{s+gr} - m_s}{\pi/4 \cdot 1.27^2 \cdot 0.5093} \quad (3)$$

Here, $m_{s+gr}$ denotes the weight of the measurement sample 10 including the graphite layer 20, and $m_s$ is the weight of the measurement sample 10 not including the graphite layer 20. 1.27 cm is the diameter of the measurement sample 10 and 0.5093 g/cm³ is the density of graphite.

Here if the thermal resistance effect of graphite layer 20 is defined as the resistance coefficient $Gr_{eff}$, it can be expressed in Equation 4.

$$Gr_{eff} = \frac{l_{apgr}}{l_{gr}} \quad (4)$$

The apparent graphite thickness $l_{apgr}$ can be found based on the information about the resistance coefficient $Gr_{eff}$. Further, as can be seen from Equation 4, if the apparent graphite thickness $l_{apgr}$ increases, the resistance coefficient increases. Further, as will be described later on, an increase in the resistance coefficient as described above decreases the half time $t_{1/2}$. A reduction in the half time is meant that the sample rapidly reaches a thermal equilibrium state and the heat 40 is rapidly dissipated from the measurement sample. It results in an increase in the thermal diffusivity α.

Figure 4:
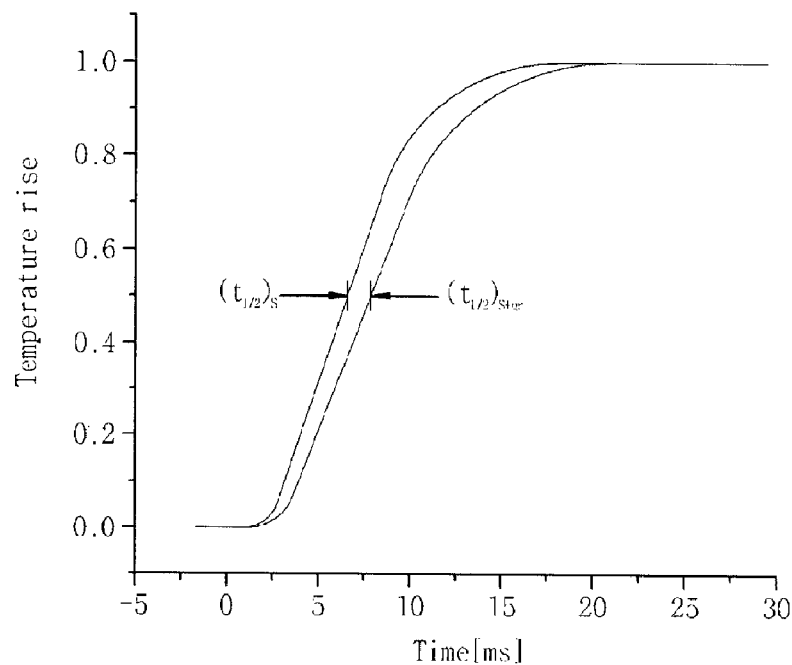
FIG. 4 is a graph showing a temperature change as time elapses depending on whether graphite coating was used according to the present invention.

FIG. 4 is a graph showing a change in the half time when the graphite layer 20 according to the present invention is coated and when the graphite layer 20 according to the present invention is not coated. From FIG. 4, it can be seen that the half time of the graphite coated sample differs from that of the graphite non-coated sample by several milliseconds. Thus, it can be seen that the coating of the graphite layer 20 acts as thermal resistance against the measurement sample 10. In the thermal diffusivity measurement device 100 using the flash method according to the present invention, the concept of the apparent graphite thickness was set as a complementary factor to a delay time depending on the coating of the graphite layer 30.

Further, the influence of the apparent graphite thickness has to be considered in calculating thermal diffusivity. Equation 5 shows that thermal diffusivity is calculated by taking the apparent graphite thickness $l_{apgr}$ and the half time $(t_{s+gr})_{1/2}$ into consideration.

$$\alpha = \frac{0.138785 (l_s + l_{apgr})^2}{(t_{s+gr})_{\frac{1}{2}}} \quad (5)$$

Here, the half time of the measurement sample 10 coated with graphite can be measured simply through the flash method. Thus, if it sought to make identical the values of thermal diffusivity before and after coating, the thickness of the coating layer has to increase together with the half time of the coated sample. The thermal diffusivity of material is a physical constant. However, the thermal diffusivity is the physical amount that may vary according to temperature and has to be measured in consideration of the influence of the temperature.

Further, the apparent graphite thickness $l_{apgr}$ can be found based on the resistance coefficient $Gr_{eff}$. The apparent graphite thickness can be said to be a virtual thickness, which represents a degree that substantially contributes to thermal diffusion in the thickness of the graphite layer 30 that is actually coated as described above.

Equation 6 can be obtained by deriving the correlation function of the resistance coefficient $Gr_{eff}$ and the half time $(t_{s+gr})_{1/2}$ on 10 standard samples. An experiment on the correlation function of the resistance coefficient and the half time was confirmed through an experiment performed on standard samples listed in Table 1. The standard samples used in this experiment include alumina, Pyroceram9606, Pyrex7790, copper, iron, Inconel600, stainless steel310, and black samples A, B with low illumination, which were supplied by NETZSCH CO., LTD.

$$Gr_{eff} = 4.2454(t_{1/2})^{-0.465} \quad (6)$$

Figure 5:
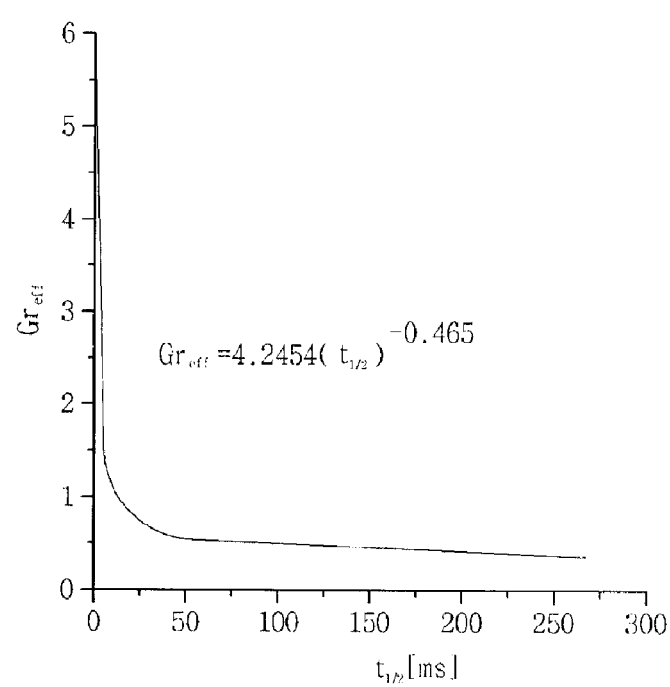
FIG. 5 is a graph showing the correlation function of the resistance coefficient and a half time according to the present invention.

FIG. 5 is a graph showing the correlation function of the resistance coefficient and a half time according to the present invention. As shown in FIG. 5, the resistance coefficient $Gr_{eff}$ shows a characteristic that it decreases as the half time $(t_{s+gr})_{1/2}$ increases.

Table 1 shows the measurement results in which the sum of the apparent graphite thickness $l_{apgr}$ and the actual graphite thickness $l_{sr}$ of the measurement sample 10 is used as an input parameter of the thickness of the measurement sample 10 when measuring the thermal diffusivity.

TABLE 1

Measurement results of thermal diffusivity and thickness of the measurement samples

| Material | $m_{gr}$ (mg) | $l_s$ (mm) | $l_{gr}$ (mm) | $t_{1/2}$ (ms) | $Gr_{eff}$ | $l_{apgr}+$ $l_s$ (mm) | $\alpha_s$ (mm²/s) | $\alpha_m$ (mm²/s) | Diff. (%) |
|---|---|---|---|---|---|---|---|---|---|
| Alumina | 0.0010 | 0.996 | 0.016 | 13.76 | 1.25 | 1.016 | 10.23 | 10.312 | −0.80 |
| Pyroceram 9606 | 0.00146 | 0.99 | 0.023 | 73.12 | 0.58 | 1.003 | 1.926 | 1.917 | 0.47 |
| Pyrex | 0.00166 | 0.986 | 0.026 | 208.5 | 0.35 | 0.995 | 0.65 | 0.648 | 0.31 |
| Iron | 0.00119 | 0.984 | 0.018 | 6.615 | 1.76 | 1.017 | 21.6 | 21.185 | 1.92 |
| Inconel600 | 0.00177 | 1.007 | 0.027 | 44.17 | 0.73 | 1.027 | 3.458 | 3.436 | 0.64 |
| Alumina | 0.0024 | 1.985 | 0.037 | 52.38 | 0.67 | 2.010 | 10.23 | 10.198 | 0.31 |
| Copper | 0.00172 | 1.004 | 0.027 | 1.681 | 3.33 | 1.093 | 117.2 | 114.726 | 2.11 |
| Copper | 0.00145 | 1.998 | 0.022 | 5.105 | 1.99 | 2.043 | 117.2 | 116.597 | 0.51 |
| Pyroceram 9606 | 0.00187 | 1.989 | 0.029 | 267.8 | 0.32 | 1.998 | 1.926 | 1.918 | 0.42 |
| stainless steel310 | 0.00157 | 1.968 | 0.024 | 154.7 | 0.41 | 1.978 | 3.352 | 3.36 | −0.24 |
| Inconel1600 | 0.0015 | 1.995 | 0.023 | 159 | 0.40 | 2.004 | 3.458 | 3.472 | −0.040 |
| Sample A | 0.00163 | 0.45 | 0.025 | 6.282 | 1.81 | 0.496 | 4.986 | 4.955 | 0.62 |
| Sample B | 0.00166 | 0.617 | 0.026 | 3.856 | 2.27 | 0.675 | 16.838 | 16.987 | −0.88 |

As shown in Table 1, the weight of the graphite layer 20 coated on the measurement sample 10 is not constant, and it is practically difficult to regularly coat graphite on the measurement sample 10. Nevertheless, it could be checked that the measured values of the thermal diffusivity $\alpha_m$ of the measurement sample 10 in all the cases is converged within an uncertainty range with respect to the value of the thermal diffusivity $\alpha_s$ of the standard sample.

Figure 6:
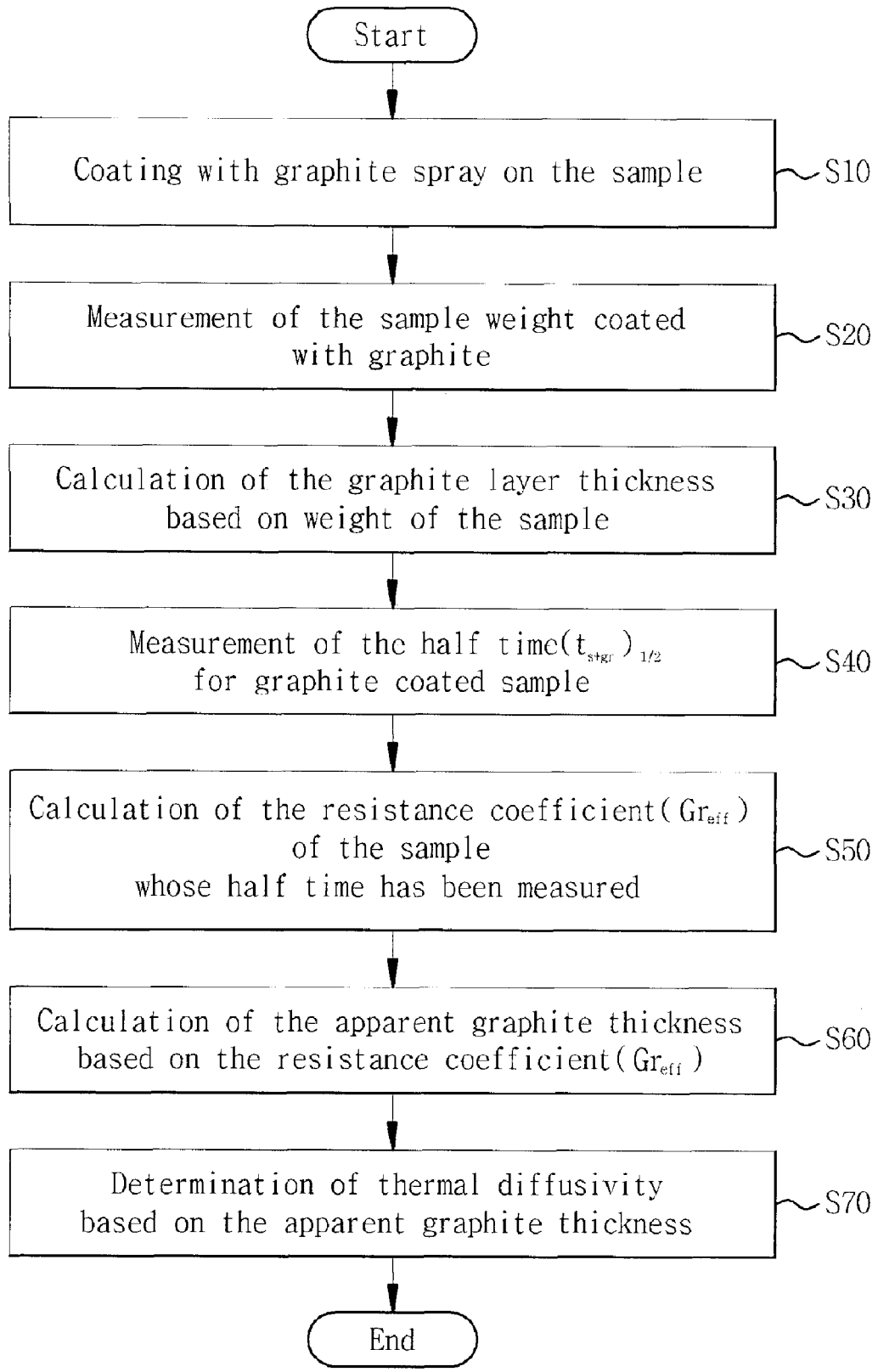
FIG. 6 is a flowchart illustrating a process of measuring thermal diffusivity according to the present invention.

FIG. 6 is a flowchart illustrating a process of measuring thermal diffusivity according to the present invention. Referring to FIG. 6, the half time $(t_{s+gr})_{1/2}$ with respect to the measurement sample 10 is experimentally calculated. That is, the half time $(t_{s+gr})_{1/2}$ is calculated based on the elapsed time from the movement of illuminating the measurement sample by flash pulse at first to that of reaching a thermal equilibrium state. However, the resistance coefficient $Gr_{eff}$ and the apparent graphite thickness $l_{apgr}$ are calculated from Equation 5 and Equation 6.

More specifically, a task of coating the measurement sample 10 with graphite is first performed (S10). This graphite coating task is performed using a spray coating method. The thickness of each of the coated graphite layers 20 is preferably in the range of 10 to 40 μm. If coating of 10 μm or less is performed, some portions that are not coated may happen. Accordingly, a problem may occur in the thermal diffusion process at the rear surface of the coated measurement sample 10. If the coated thickness of the measurement sample 10 is 40 μm or more, the coating state of the coating layer differs depending on the location of the sample, which hinders accurate measurement of the thermal diffusivity $\alpha$.

A weight of the measurement sample 10 which is coated with the graphite layer 20 is measured (S20). The thickness of the graphite layer 20 can be calculated based on the weight of the measurement sample 10 according to Equation 3 (S30). A temperature change at the rear surface of the coated sample 10 whose thickness has been calculated depending on the time is measured using the infrared sensor 70. The method of measuring a temperature change at the rear surface of the measurement sample 10 depending on the time using the infrared sensor 70 is evident to those having ordinary skill in the art and description thereof is omitted. The half time $(t_{s+gr})_{1/2}$ is calculated based on the temperature change at the rear surface of the measurement sample 10 depending on the time (S40).

After the half time $(t_{s+gr})_{1/2}$ is calculated, the resistance coefficient $Gr_{eff}$ of the measurement sample 10 is calculated by Equation 6 (S50). The experiment has shown that the thermal diffusivity $\alpha$ can be found accurately within an uncertain range although the resistance coefficient is calculated using Equation 6. If the resistance coefficient $Gr_{eff}$ is calculated as described above, the apparent graphite thickness $l_{apgr}$ can be calculated based on Equation 4 since it can be said that the resistance coefficient $Gr_{eff}$ is the ratio of the apparent graphite thickness $l_{apgr}$ and the coated graphite thickness $l_{gr}$ (S60).

After the apparent graphite thickness $l_{apgr}$ is calculated, the thermal diffusivity $\alpha$ is calculated based on Equation 5 (S70). Accordingly, the thermal diffusivity $\alpha$ of each measurement sample 10 can be measured.

Although the thermal diffusivity of the measurement sample 10 has so far been measured through various modelings, the measurement results of the thermal diffusivity using other methods have a great error. However, the measurement results of the thermal diffusivity using the flash method according to the present invention can solve this mismatch by employing a method of setting the apparent graphite thickness $l_{apgr}$ that contributes to thermal resistance.

According to the method of measuring thermal diffusivity using the flash method in accordance with the present invention, an apparent graphite thickness with respect to the thickness of a graphite layer is set, the resistance coefficient of a sample is found based on the set apparent graphite thickness, and the correlation function of the resistance coefficient and the thermal diffusivity is induced.

Accordingly, the thermal diffusivity of a measurement sample can be detected accurately based on the induced correlation function. Consequently, electrical products and mechanical components can be designed on the basis of accurate thermal physical properties in the applications of various electrical or mechanical components.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An apparatus for measuring thermal diffusivity using the flash method, the apparatus comprising:
   a laser generator for generating a flash beam;
   a measurement sample having graphite layers formed on front and rear surfaces thereof and interposed in a path of the flash beam, the front surface being proximate to the laser generator and the rear surface being remote therefrom;
   an infrared sensor disposed at the rear of the measurement sample for measuring a temperature and time at the rear surface of the measurement sample from heat dissipated from the measurement sample, the infrared sensor generating an output signal as a function of said temperature and time; and
   operation means coupled to the infrared sensor for performing an operation based on the output signal of the infrared sensor, the operation means calculating a half time $(t_{s+gr})_{1/2}$ based on the output signal, said half time being the time required for the occurrence of half of the temperature rise for the measurement sample to reach thermal equilibrium, the operation means calculating a resistance coefficient $Gr_{eff}$ of the measurement sample as a function of said half time, the operation means calculating an apparent graphite thickness $l_{apgr}$ of the measurement sample as a function of said resistance coefficient, the operation means calculating the thermal diffusivity of the measurement sample as a function of said apparent graphite thickness.

2. The apparatus as claimed in claim 1, wherein the measurement sample is supported by sample holders and covered with a sample cover to thereby maintain an insulation state.

3. The apparatus as claimed in claim 1, wherein each of the graphite layers respectively formed on the front and rear surfaces of the measurement sample has a thickness of 10 μm to 40 μm.

4. The apparatus as claimed in claim 1, wherein the graphite layers respectively formed on the front and rear surfaces of the measurement sample are coated with graphite through spray coating.

5. A method of measuring thermal diffusivity using the flash method, the method comprising:
   coating a measurement sample with graphite through spray to thereby form graphite layers;
   measuring a thickness and weight of the graphite-coated measurement sample;
   calculating a thickness $l_{gr}$ of the formed graphite layer based on the measured thickness and weight of the measurement sample;
   calculating a half time $(t_{s+gr})_{1/2}$ with respect to the graphite-coated measurement sample;
   calculating a resistance coefficient of the measurement sample whose half time $(t_{s+gr})_{1/2}$ has been calculated;
   calculating an apparent graphite thickness $l_{apgr}$ based on the resistance coefficient $Gr_{eff}$; and
   calculating a thermal diffusivity α based on the apparent graphite thickness $l_{apgr}$.

6. The method as claimed in claim 5, wherein the half time $(t_{s+gr})_{1/2}$ is experimentally calculated from a temperature rise graph at the rear surface of the measurement sample depending on the time.

7. The method as claimed in claim 5, wherein the resistance coefficient $Gr_{eff}$ is calculated by the following Equation 6:

$$Gr_{eff} = 4.2454(t_{1/2})^{-0.465} \tag{6}$$

wherein $t_{1/2}$ is the time required for the occurrence of half of the temperature rise to reach the thermal equilibrium.

8. The method as claimed in claim 5, wherein the apparent thickness $l_{apgr}$ is calculated by the following Equation 4:

$$Gr_{eff} = \frac{l_{apgr}}{l_{gr}}. \tag{4}$$

9. The method as claimed in claim 5, wherein the thermal diffusivity α is calculated by the following Equation 5:

$$\alpha = \frac{0.138785 \, (l_s + l_{apgr})^2}{(t_{s+gr})_{1/2}} \tag{5}$$

wherein $l_s$ is the thickness of the graphite coated measurement sample.

* * * * *